(12) United States Patent
Vukic et al.

(10) Patent No.: US 8,672,193 B2
(45) Date of Patent: Mar. 18, 2014

(54) METERING DISPENSER

(75) Inventors: Mathey Vukic, Baar (CH); Andy Greter, Baar (CH)

(73) Assignee: Medmix Systems AG, Rotkreuz (CH)

( * ) Notice: Subject to any disclaimer, the term of this patent is extended or adjusted under 35 U.S.C. 154(b) by 0 days.

(21) Appl. No.: 13/384,536

(22) PCT Filed: Jun. 21, 2010

(86) PCT No.: PCT/CH2010/000159
§ 371 (c)(1),
(2), (4) Date: Jan. 17, 2012

(87) PCT Pub. No.: WO2011/009221
PCT Pub. Date: Jan. 27, 2011

(65) Prior Publication Data
US 2012/0111897 A1    May 10, 2012

(30) Foreign Application Priority Data
Jul. 22, 2009    (CH) ...................................... 1151/09

(51) Int. Cl.
*B67D 7/60*    (2010.01)
(52) U.S. Cl.
USPC ............................. 222/391; 222/326; 222/137
(58) Field of Classification Search
USPC ........................................ 222/326, 391, 137
See application file for complete search history.

(56) References Cited

U.S. PATENT DOCUMENTS

| | | | |
|---|---|---|---|
| 2,732,102 A * | 1/1956 | Ekins | 222/327 |
| 4,456,450 A * | 6/1984 | Heling | 425/376.1 |
| 4,744,494 A | 5/1988 | Seager et al. | |
| 5,192,008 A * | 3/1993 | Hwan | 222/391 |
| 5,248,068 A * | 9/1993 | Goergen et al. | 222/326 |
| 5,370,273 A * | 12/1994 | Rohloff et al. | 222/132 |
| 5,400,925 A * | 3/1995 | Simmen | 222/137 |
| 5,464,131 A | 11/1995 | Keller | |
| 5,499,548 A * | 3/1996 | Keller | 74/96 |
| 5,501,374 A * | 3/1996 | Laufer et al. | 222/391 |
| 5,992,694 A | 11/1999 | Keller | |

(Continued)

FOREIGN PATENT DOCUMENTS

| | | |
|---|---|---|
| CH | 641 736 A5 | 3/1984 |
| GB | 1198214 A5 | 7/1970 |

*Primary Examiner* — Paul R Durand
*Assistant Examiner* — Donnell Long
(74) *Attorney, Agent, or Firm* — Sughrue Mion, PLLC

(57) ABSTRACT

The invention relates to a dispenser for discharging at least one component. Said dispenser comprises a base body (100) and an advancing element (300) that can be slid. The advancing element (300) acts upon a container having the component so that the component is discharged from the container by means of an advancement of the advancing element (300). The advancing element (300) comprises teeth (321) in the advancing direction. An actuating lever (400) can be swiveled relative to the base body (100) between an initial position and an activated position. The actuating lever comprises one or more teeth (421), which are engaged with the teeth (321) of the advancing element when the advancing element (300) is advanced. In order to enable a simple resetting motion of the actuating lever (400) from the activated position back to the initial position, the actuating lever (400) can be moved as a whole to a decoupled position relative to the base body (100), in which decoupled position the teeth (421) of the actuating lever (400) disengage from the teeth (321) of the advancing element (300). A very simple design of the dispenser having few individual parts is thereby enabled.

15 Claims, 4 Drawing Sheets

(56) References Cited

U.S. PATENT DOCUMENTS

| | | | |
|---|---|---|---|
| 6,047,861 A * | 4/2000 | Vidal et al. | 222/137 |
| 6,439,439 B1 * | 8/2002 | Rickard et al. | 222/391 |
| 6,450,370 B2 | 9/2002 | Keller | |
| 6,585,696 B2 | 7/2003 | Petersen et al. | |
| 6,672,489 B1 * | 1/2004 | Huang | 222/391 |
| 6,929,157 B2 * | 8/2005 | Orecchia et al. | 222/326 |
| 6,945,436 B2 * | 9/2005 | Mayer | 222/391 |
| 2008/0114315 A1 | 5/2008 | Voegele et al. | |

* cited by examiner

METERING DISPENSER

CROSS REFERENCE TO RELATED APPLICATION

This application is a National Stage of International Application No. PCT/CH2010/000159, filed on Jun. 21, 2010, claiming priority based on Swiss Patent Application No. 01151/09, filed Jul. 22, 2009, the contents of all of which are incorporated herein by reference in their entirety.

TECHNICAL FIELD

The present invention relates to a dispensing device in which an advancing element is advanced step by step by the actuation of a lever, in order to dispense at least one component from the dispensing device. Such a dispensing device is also referred to as a metering dispenser.

PRIOR ART

Various types of metering dispensers are known from the prior art, most of them being designed like a pistol. Such metering dispensers are used to dispense one or more components from a container, which is in most cases designed in the form of a single or double syringe or of a corresponding cartridge.

Thus, U.S. Pat. No. 5,992,694 discloses a metering dispenser of the type mentioned, in which two components are present in two different syringe bodies of a cartridge. Syringe plungers are movable in the syringe bodies, in order to dispense the components from the syringe bodies. An advancing element in the form of a double thrust rod is used to advance the syringe plungers in the syringe bodies. This advancing element has a toothing on its underside. The metering dispenser has a pistol-like handle. An actuating lever is articulated pivotably on the handle. When the actuating lever is pressed in the direction of the handle, it acts on a toothed driver element, which is in engagement with the double thrust rod and advances the latter. When the actuating lever is then let go again, it returns to its initial position under the effect of a spring force. During this movement, the driver element executes a pivoting movement and disengages from the toothing with the double thrust rod. Between the actuating lever and the driver element, a compensating link is articulated in a rotatably movable manner in order to compensate for the arc movement of the actuating lever across the course of the actuating movement. In this way, relative movements between the teeth of the driver element and the teeth of the double thrust rod are avoided. However, this also results in a relatively complicated design of the metering dispenser.

U.S. Pat. No. 5,464,131 likewise discloses a metering dispenser of the type described. The actuating lever of this dispenser is articulated with its pivot axis on two blocks that are vertically displaceable in the dispenser. The actuating lever is additionally articulated with one end on a driving dog, which is guided in a horizontally displaceable manner in the dispenser and which engages with the double thrust rod. When the actuating lever is actuated, its pivoting movement displaces the driving dog and thus pushes the double thrust rod forward in the direction of advance. In order to compensate for the unavoidable arc movement of the point at which the driving dog is articulated, the pivot axis of the actuating lever moves downward by means of the displaceable blocks. When the actuating lever is let go again, it is spring-loaded back into its initial position. On account of an asymmetrical configuration of the toothing, the driving dog slides rearward again into the initial position, while the double thrust rod remains stationary. This mechanism too is quite complicated and requires a considerable number of individual parts.

US 2008/0114315 discloses a dispenser in which the actuating lever interacts directly with a toothing of an advancing rod. For this purpose, the lever evidently has a spring-loaded, telescopic driver which, during the return movement of the lever to its initial position, slides over the asymmetrically configured toothing of the advancing rod.

GB 1 198 214 discloses a dispenser in which a driving pawl is articulated pivotably on the actuating lever and is spring-loaded in the direction of an advancing rod with a toothing. During the return movement of the actuating lever, the driving pawl slides over the asymmetrically configured toothing. A mechanism with a spring-loaded pawl is also disclosed in U.S. Pat. No. 6,585,696.

However, all of the abovementioned dispensers have a relatively complicated design and consist of a large number of parts. Consequently, they are, inter alia, unsuitable for single use as disposable articles.

U.S. Pat. No. 4,744,494 discloses a dispenser in which an actuating lever is provided that is pivotable relative to a housing and, during pivoting, engages by means of a flexible tooth in the locking teeth of an advancing element and thus pushes the latter forward. When the actuating lever is subsequently let go, the flexible tooth slides over the locking teeth of the advancing element until it disengages therefrom. However, because the tooth of the advancing element is flexible, the maximum force that can be transferred from the actuating lever to the advancing element is limited.

SUMMARY OF THE INVENTION

It is therefore an object of the present invention to provide a dispensing device of the type of a metering dispenser, which is of simple design, can be produced inexpensively and is suitable in principle for production as a disposable article for single use.

This object is achieved by a dispensing device (a dispenser) for dispensing at least one component is thus made available, comprising the following:
  a base body;
  an advancing element, which is guided displaceably relative to the base body and is designed to act on a container containing the component such that the component is dispensed from the container by means of an advance of the advancing element in a direction of advance, wherein the advancing element has a toothing along the direction of advance (i.e. the advancing element has a multiplicity of teeth along the direction of advance);
  an actuating lever, which is pivotable relative to the base body between an initial position and an activated position and has one or more teeth, which are suitable for engaging with the toothing of the advancing element, such that the advancing element can be moved in the direction of advance by a pivoting movement of the actuating lever.

Here, the actuating lever as a whole is displaceable relative to the base body between an engagement position, in which the teeth of the actuating lever are in engagement with the toothing of the advancing element, and a decoupled position, in which the teeth of the actuating lever are disengaged from the toothing of the advancing element.

When the actuating lever is pivoted from the initial position to the activated position, the actuating lever is thus situated with its teeth in engagement with the toothing of the advancing element and pushes the advancing element by a defined amount in the direction of advance. In this process, a predetermined quantity (dose) of the component is dispensed, and this quantity can be predefined by the range of pivoting of the lever and by the lever step-down ratio. The dispenser can therefore also be designated as a metering dispenser. When the actuating lever is thereafter moved back from the activated position to the initial position, the advancing element is intended to remain stationary. For this purpose, the teeth of the actuating lever disengage from the toothing of the advancing element. In the present invention, this is permitted by the fact that, relative to the base body, the entire actuating lever is movable, in particular pivotable, toward the toothing and away from the toothing. The actuating lever preferably forms a rigid, dimensionally stable unit, and the teeth of the actuating lever are preferably immovable relative to the rest of the actuating lever. They can in particular be formed integrally on the actuating lever.

In particular, during the movement of the actuating lever as a whole, the position of the pivot axis changes, i.e. the position of the imaginary line about which the pivoting movement of the actuating lever takes place. The actuating lever is thus characterized in that, relative to the base body, its pivot axis is movable toward the toothing and away from the toothing. This can be achieved by the fact that the actuating lever has a shaft element, which is guided displaceably on the base body. However, the mobility as a whole can also be achieved other than by such a shaft element, e.g. via a slotted guide.

Since the actuating lever as a whole is displaceable relative to the base body, it is possible to avoid complicated measures for compensating the arc movement, such as those that have been proposed in the prior art, for example a driving dog, a telescopic area of the lever on which the teeth are formed, or a pivotable driving pawl that is connected to the lever. The structure of the dispenser is thus greatly simplified. Such a dispenser can be produced from a small number of inexpensive parts and can in particular be provided as a disposable product. This is advantageous especially in medical applications, since the dispenser can already be sterilized at the place of manufacture and supplied in a sterile state. Complicated sterilization by the user, as is in most cases necessary in the case of reusable dispensers in the medical field, can thus be avoided.

In order to permit an automatic resetting of the actuating lever, the actuating lever is preferably spring-loaded in the direction of the initial position. Moreover, the actuating lever as a whole, in particular its pivot axis, is preferably spring-loaded in the direction of the engagement position, in order to ensure that the lever is in engagement with the toothing of the advancing element during the movement from the initial position to the activated position. Each of these functions can be performed respectively by a separate spring. However, these two functions are preferably performed jointly by a common spring, which generates a first force component, in order to load the actuating lever in the direction of the initial position, and also a second force component, in order to load the actuating lever in the direction of the engagement position. Of course, several such springs can be provided parallel to one another in order to increase the spring force and achieve redundancy. The springs used can be any types of springs known from the prior art, in particular a leaf spring bent in a V-shape, wherein one leg of the leaf spring engages on the base body and the other leg engages on the actuating lever, a spiral spring with one free end engaging on the base body and the other free end engaging on the actuating lever, a coil spring that is mounted in a suitable orientation between base body and actuating lever and can act with tension or pressure, etc.

In order to ensure that, during the resetting movement of the actuating lever, the advancing element is not driven back counter to the direction of advance, the dispensing device preferably also has a return stop mechanism, which permits a movement of the advancing element in the direction of advance but at least impedes, preferably completely prevents, a movement thereof counter to the direction of advance. This prevents a reverse movement of the advancing element during the return movement of the actuating lever from the activated position to the initial position. For this purpose, the return stop mechanism preferably has a blocking element, which is suitable for engaging in the toothing of the advancing element and which, relative to the base body, is spring-loaded in the direction of the toothing. The blocking element can be, for example, a carriage that is displaceable relative to the base body, has one or more teeth, and is loaded by a compression spring in the direction of the toothing of the advancing element. Alternatively, for example, it is also conceivable to use a spring-loaded, pivotable locking pawl or a spring arm with an engagement element at its free end, as is known in many different forms from the prior art.

In order to permit a secure advance and at the same time a particularly simple resetting of the advancing element, the teeth of the toothing of the advancing element are preferably asymmetrically configured, i.e. each tooth has a front flank, which faces in the direction of advance, and a rear flank, which faces in a direction counter to the direction of advance, wherein the front flank assumes a shallower angle to the direction of advance than the rear flank. A particularly secure advance is permitted if the rear flank assumes an angle of more than 90° to the direction of advance, i.e. if the teeth are hook-shaped, such that the rear flank faces with its normal vector toward the advancing element itself.

In order to permit simple handling, the base body preferably has a handle shaped like a pistol grip and designed to be grasped in one hand by a user, and the actuating lever has an actuating area designed to be pulled by one or more fingers of this hand in the direction of the handle, in order to pivot the actuating lever from the initial position to the activated position. Related designs of the grip area as an elongate lever arm, as a circular ring or a ring of any desired shape, etc., are known per se from the prior art.

The teeth of the actuating lever are preferably arranged, in relation to the (imaginary) pivot axis, on a top face of the actuating lever lying opposite the grip area (in particular, the actuating area and an area on which the teeth are arranged are thus formed on opposite lever arms with respect to the pivot axis), and the toothing of the advancing element is arranged on an underside of the advancing element facing toward the handle. The actuating lever is therefore moved downward when it disengages from the advancing element. It is also conceivable, however, for the toothing to be arranged differently. For example, it is conceivable that the toothing is arranged on the top face of the advancing element facing away from the handle, and that the actuating lever engages laterally around the advancing element in such a way that its teeth engage in this toothing from above. The actuating lever then moves upward when the teeth disengage from the toothing.

In a particularly simple embodiment, the actuating lever has at least one shaft element, which is guided displaceably in at least one oblong hole of the base body, in order to move the actuating lever as a whole between the engagement position and the decoupled position. The oblong hole can be open in one direction, in particular toward the bottom, so as to be able to connect the actuating lever particularly easily to the base body. However, it can also be closed at both of its ends. In this case it is conceivable that, during assembly, a shaft element is pushed laterally through the oblong hole. However, it is also possible that such oblong holes are present, for example, on two side walls of the base body and that the actuating lever, with its integrally formed and spring-loaded shaft elements, is clicked into these oblong holes counter to a spring force, if appropriate with the aid of suitable guide grooves that are provided on the inner face of the base body and lead from an edge of the base body to the oblong hole. Alternatively, it is also possible, for example, for the overall shaft element to be guided in guide grooves shaped like oblong holes on the base body. However, instead of being arranged on the actuating lever, a shaft element can also be formed on the base body, and the actuating lever can accordingly have an oblong hole or guide grooves.

Preferably, the dispensing device also comprises a container for receiving the component(s). This container is preferably designed as a cylindrical syringe body for receiving the at least one component, with a syringe plunger movable in the syringe body, wherein the syringe plunger can be pushed forward in the syringe body by the advancing element in order to dispense the component. However, the container can also have another form. The container, in particular the syringe body, is preferably formed integrally with the base body, which further reduces the production costs and which avoids possible undesired play between dispenser and container.

In preferred embodiments, the dispenser is a multi-component dispenser for simultaneously dispensing two or more components, which are subsequently mixed in a mixer. For this purpose, the dispenser has at least a first cylindrical syringe body, with a first syringe plunger movable therein, and a second cylindrical syringe body arranged parallel to the first syringe body, with a second syringe plunger movable in the second cylindrical syringe body. The syringe bodies can be designed separately from each other or can be connected to each other in the manner of a cartridge. They are preferably formed integrally with the base body.

The advancing element then preferably comprises at least a first plunger rod, which acts with a distal end on the first syringe plunger, a second plunger rod, which acts with a distal end on the second syringe plunger, and a connection area between the plunger rods, which connection area is formed in a proximal end area of the plunger rods, in order to connect the plunger rods to each other. The plunger rods can bear loosely on the syringe plungers or can be connected to the latter. In a design that saves material, the toothing of the advancing element is formed directly on the first and on the second plunger rod. However, it is also possible for a separate ram to be present with the toothing, which ram extends parallel to the two plunger rods.

The base body preferably forms a housing through which the advancing element extends. In an advantageous embodiment, the advancing element is guided displaceably in a guide element, which is designed separately from the base body and which can be secured on the base body. The guide element can in particular be pushed into the housing formed by the base body. The aforementioned return stop mechanism can be formed integrally on the guide element or separate therefrom. In particular, the return stop mechanism can comprise one or more spring arms, which are formed integrally on the guide element and whose free ends each have an engagement structure for engagement in the toothing of the guide element. However, the advancing element can also be guided displaceably directly on the base body itself.

BRIEF DESCRIPTION OF THE DRAWINGS

Preferred embodiments of the invention are described below with reference to the drawings, which serve only for explanatory purposes and are not to be interpreted as limiting the invention. In the drawings.

DESCRIPTION OF PREFERRED EMBODIMENTS

Figure 1:
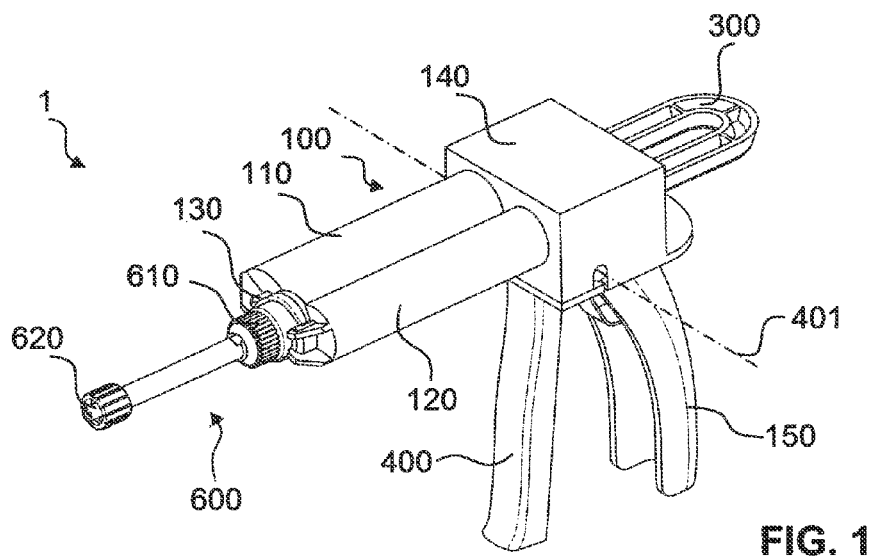
FIG. 1 shows a perspective view of a metering dispenser with a mixer secured thereon.

FIG. 1 shows a dispensing device according to the invention in the form of a metering dispenser. The metering dispenser 1 has a base unit 100, which comprises a cuboid, hollow main body 140, a first syringe body 110, a second syringe body 120, and a pistol-like handle 150. The syringe bodies are connected to each other and are connected jointly to the main body 140. The handle 150 extends downward from the main body 140. At the front (distal) end of the two syringe bodies 110, 120, there is a fastening area 130 on which a mixer 600 is secured. For this purpose, the rear (proximal) end of the mixer 600 has a first, proximal fastening area, which is designed to match the fastening area 130 of the base unit. At its front, distal end, the mixer has a second, distal fastening area 620 which, in the present example, is designed as a Luer lock. The mixer ensures that two different components stored in the syringe bodies 110, 120 are mixed with each other in a manner known per se after being discharged from the syringe bodies, and the mixture is dispensed at the distal end of the mixer. An advancing element 300 is guided displaceably in the base unit 100. The advancing element 300 can be advanced in the distal direction by an actuating lever 400.

Figure 2:
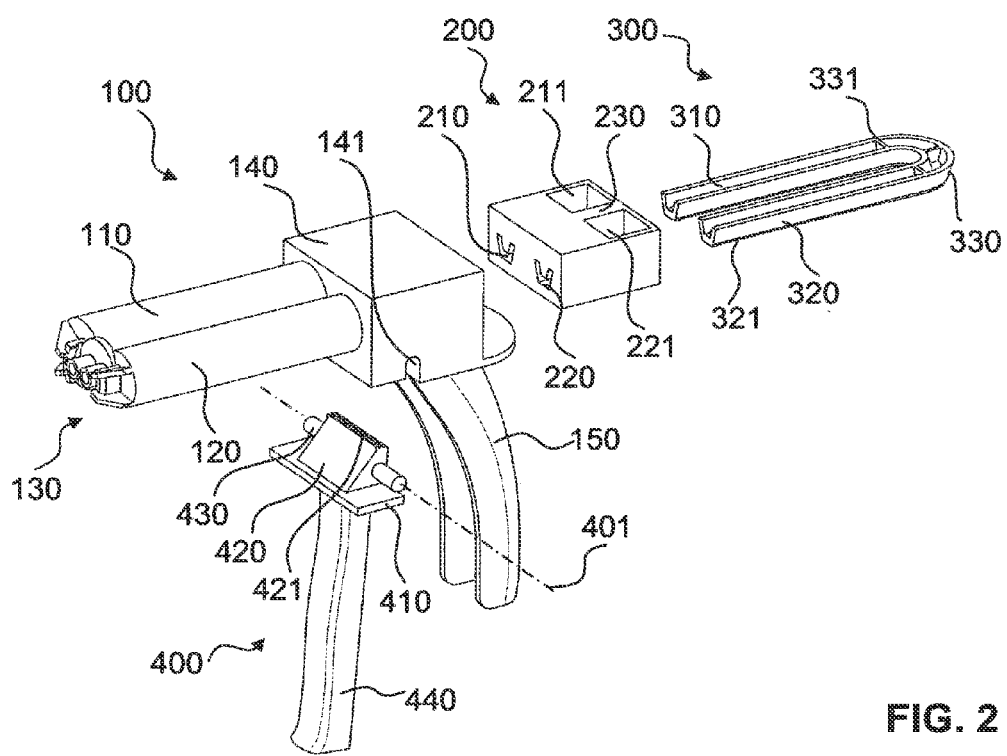
FIG. 2 shows an exploded view of different parts of the metering dispenser from FIG. 1.
Figure 3:
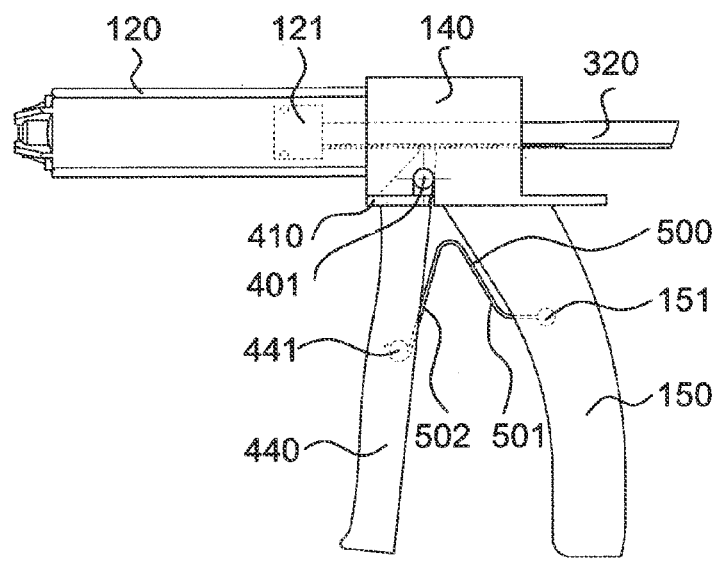
FIG. 3 shows a side view of the metering dispenser from FIG. 1.

FIG. 2 shows the main parts of the metering dispenser in a disassembled state. A guide element 200, in which the advancing element 300 is guided, can be pushed into the cuboid main body 140 from the direction of the proximal end. The main body 140 forms a housing for the guide element 200 and receives the latter in its entirety. The guide element 200 is in turn cuboid itself. In the direction of advance, the guide element has two parallel and continuous guide openings 210, 220 with a U-shaped or V-shaped cross section. Two parallel access openings 211, 221 extend perpendicularly thereto in the vertical direction. A partition wall 230 extending in the direction of advance and in the vertical direction is formed between the access openings.

The advancing element 300 has a first plunger rod 310 and a second plunger rod 320. The plunger rods have a U-shaped or V-shaped cross section that corresponds to the cross section of the guide openings 210, 220 of the guide element 200. The plunger rods can thus be pushed in a guided manner into the guide element 200. At their rear, proximal end, the plunger rods are connected to each other via a U-shaped connection area 300. In this area, the advancing element is reinforced by several reinforcement walls 331. On their underside, the plunger rods 310, 320 have a toothing, which is described in more detail below.

The actuating lever 400 has a main plate 410, from which an actuating area 440 extends downward. A wedge-shaped carrier 420 extends upward from the main plate 410. On its top face, the carrier 420 has several teeth 421, which are described in more detail below. A shaft element 430 protrudes laterally from both sides of the carrier 420. This can be a shaft element that is pushed in through the carrier and that can be made of metal, for example. However, the shaft element is preferably formed integrally with the lever 400 and is in this case formed by two pins protruding laterally from the carrier 420 on opposite sides.

The main body 140 is open toward the bottom in its front area. Two recesses 141 formed in the side walls of the main body 140 have the shape of an inverted U and each form an oblong hole open toward the bottom. The shaft element 430 of the actuating lever 400 can be pushed from underneath into the recesses 141.

FIGS. 3 to 6 show different views of the metering dispenser in its initial state. The guide element 200 is pushed from the direction of the proximal end into the main body 140 of the base unit 100 and fixed in this position. The actuating lever 400 is pushed from underneath into the recesses 141. A spring 500 serves, on the one hand, to press the actuating lever 400 as a whole upward into the recesses 141 and, on the other hand, to press the actuating area 440 of the lever 400 forward into the initial position. For this purpose, the spring 500 has a first leg 501 and a second leg 502, which together form the shape of an inverted V. The free end of the first leg 501 is fixed on the handle 150 at a fastening location 151 in such a way that the spring 500 is neither displaceable nor pivotable in this area. The free end of the second leg 502 engages loosely at a fastening location 441 of the actuating area 440. The spring is pretensioned in such a way that it generates a forward force component, in order to press the actuating area 440 of the actuating lever 400 forward, and also generates an upward force component, in order to press the shaft 430 of the actuating lever 400 upward into the recesses 141. As can be seen particularly clearly in FIG. 6, the top face 411 of the main plate 410 bears on the bottom edge 142 of the main body 140 and thus forms an abutment that limits the range of movement of the actuating lever forward and upward.

Figure 4:
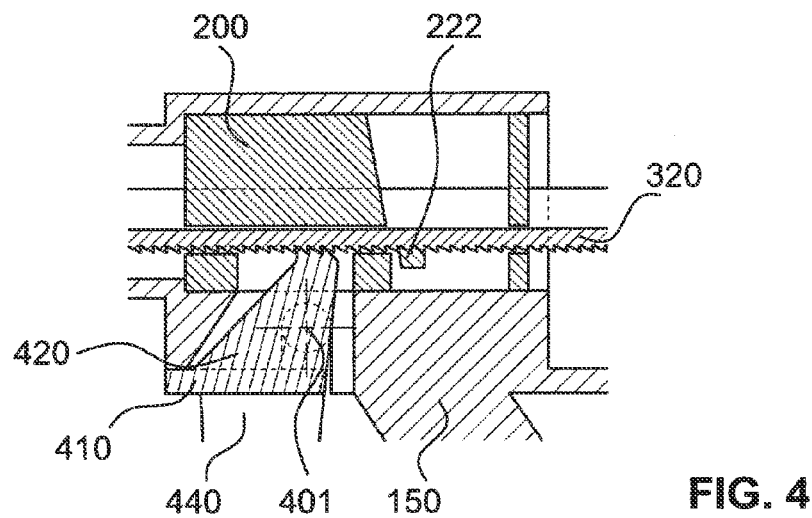
FIG. 4 shows a detail from a longitudinal section through the metering dispenser from FIG. 1, in a plane extending centrally through the second syringe body.
Figure 5:
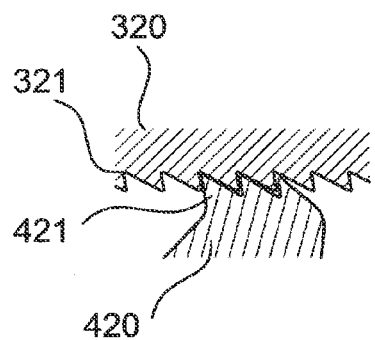
FIG. 5 shows a detail from FIG. 4 in the area of the engagement between advancing element and actuating lever.
Figure 6:
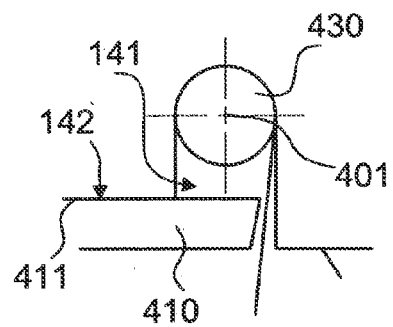
FIG. 6 shows a detail from FIG. 3 in the area of the pivot axis of the actuating lever.
Figure 7:
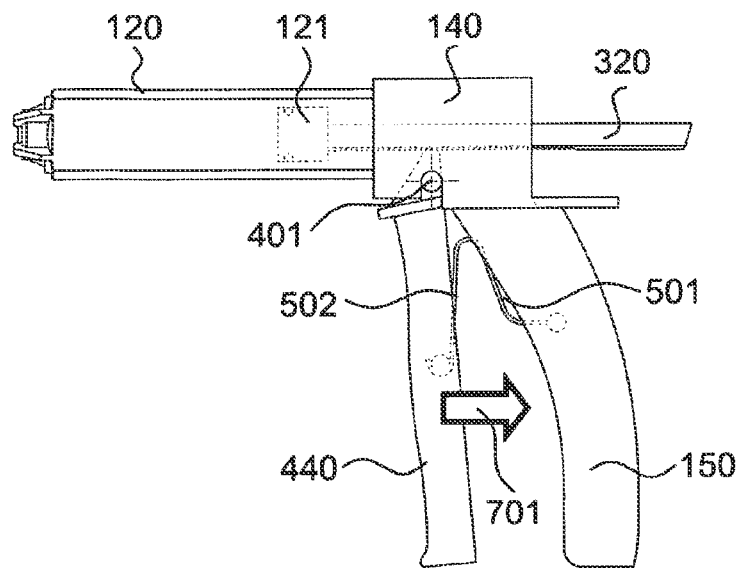
FIG. 7 shows a side view of the metering dispenser from FIG. 1 in an activated state.
Figure 8:
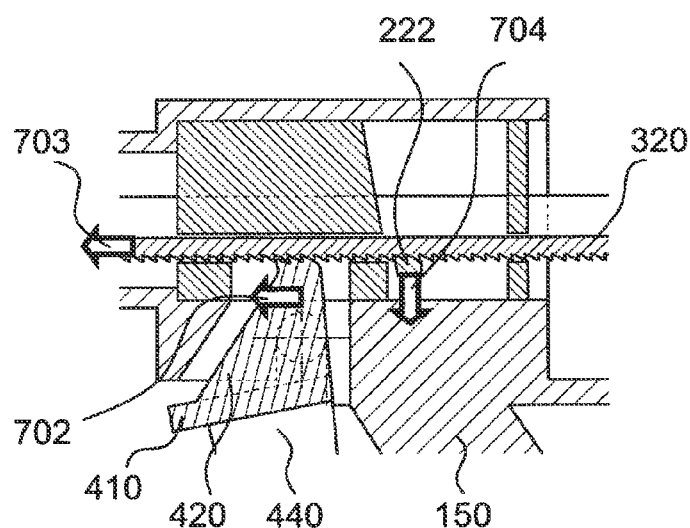
FIG. 8 shows a detail from a longitudinal section through the metering dispenser in the state in FIG. 7, in a plane extending centrally through the second syringe body.
Figure 9:
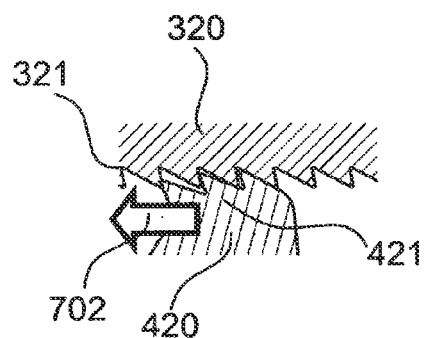
FIG. 9 shows a detail from FIG. 8 in the area of the engagement between advancing element and actuating lever.
Figure 10:
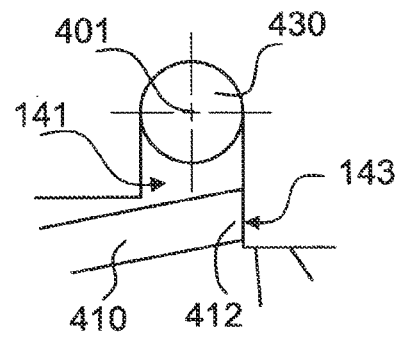
FIG. 10 shows a detail from FIG. 7 in the area of the pivot axis of the actuating lever.
Figure 11:
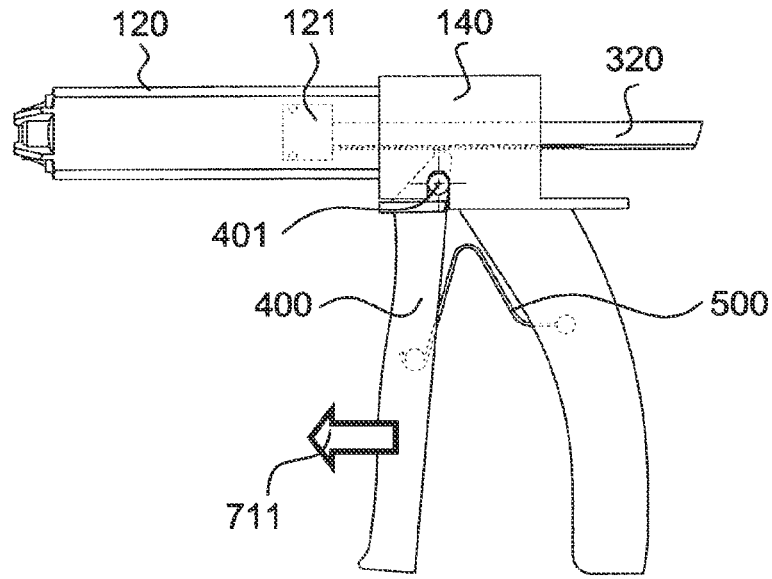
FIG. 11 shows a side view of the metering dispenser after the actuating lever has been let go.

As can be seen in particular from FIGS. 4 and 5, the teeth 421 of the actuating lever 400 engage, in the initial position, both with the toothing 321 of the second plunger rod 320, shown here, and also with the corresponding toothing of the first plunger rod 310. The teeth of the two plunger rods 310, 320 are configured asymmetrically. Each of the teeth has a front flank, which is relatively shallow to the direction of advance, and a rear flank, which is almost perpendicular to the direction of advance and, in the present example, even assumes an angle of more than 90° to the direction of advance. In other words, the teeth are designed like barbs. A normal vector on the rear flank has a component facing upward toward the advancing element. The teeth 421 on the top face of the actuating lever 400 are accordingly of a matching configuration. As can be seen from FIG. 5, these teeth are arranged along an arc or sector of a circle whose radius corresponds to the distance of the teeth from the pivot axis.

Two blocking elements formed on the guide element 200 likewise have teeth on their top face and engage from underneath in the toothing in the two plunger rods 310, 320. Of these, FIG. 4 shows only the second blocking element 222. The latter has the form of a spring arm which is designed integrally with the guide element and of which one end is secured on the partition wall 230, while the other, free end has the teeth and is thus designed as an engagement element for engaging with the toothing 321 of the plunger rod 320. The spring arm generates an upwardly directed spring force, such that the blocking element 222 is pretensioned in the direction of the toothing 321 of the plunger rod 320. A corresponding further blocking element also cooperates with the first plunger rod 310. As a result of the asymmetrical configuration of the toothing on the two plunger rods, the blocking elements, acting in the manner of a ratchet connection, permit an advance movement of the plunger rod in the direction of advance but prevent a return movement in the opposite direction. Of course, the blocking element 222 can also be designed differently, for example in the manner of a spring-loaded, pivotable catch.

FIGS. 7 to 10 show the metering dispenser in an activated position. The metering dispenser has now been grasped by a user via the handle 150, and the actuating area 440 of the actuating lever 400 has been pulled by the fingers of this hand toward the handle 150 in the actuating direction 701. In this way, the teeth 421 on the top face of the actuating lever move by a relatively small amount, defined by the lever step-down ratio, in a direction 702 that is counter to the actuating direction 701. Strictly speaking, the teeth 421 execute an arc-shaped movement about the pivot axis. In doing so, the teeth 421 drive the second plunger rod 320 via the toothing 321, and also drive the first plunger rod 310 via the corresponding toothing, in the direction of advance 703. The plunger rod 320 bears with its free, distal end on a syringe plunger 121 which, by means of this movement, is pushed forward in the distal direction. In this way, the component located in the second syringe body 120 is dispensed from the latter. The same procedure also takes place correspondingly in the first syringe body 110. The emerging components can now be fed to a mixer, e.g. the mixer 600 illustrated in FIG. 1.

During the advance movement of the plunger rod 320, the plunger rod 320 slides over the blocking element 222, with the blocking element executing a deflection movement in the direction 704. As is shown in particular in FIG. 10, the pivot axis of the actuating lever 400 remains in its upper position during the entire dispensing movement, and the teeth 421 of the actuating lever accordingly remain in engagement with the toothing 321 of the plunger rod during the entire advance movement. The advance movement is limited by the fact that the rear face 412 of the main plate 410 abuts against a front edge 143 of the main body 140, which front edge 143 is formed in the area of the recess 141. The abutment thus formed limits the range of pivoting of the actuating lever 400.

Figure 12:
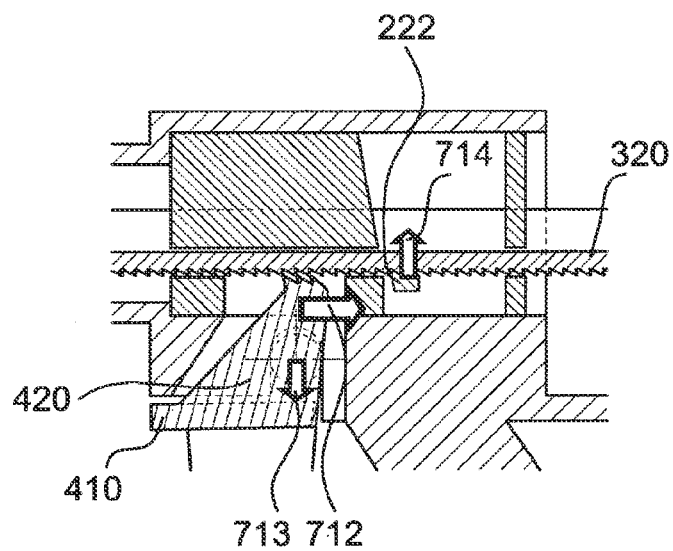
FIG. 12 shows a detail from a longitudinal section through the metering dispenser in the position in FIG. 11, in a plane extending centrally through the second syringe body.
Figure 13:
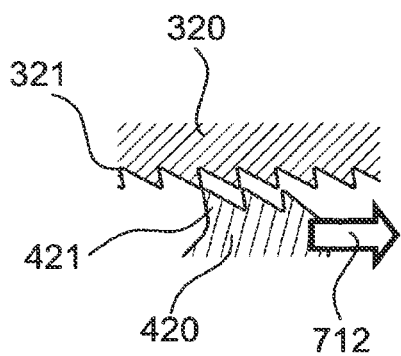
FIG. 13 shows a detail from FIG. 12 in the area of the engagement between advancing element and actuating lever.
Figure 14:
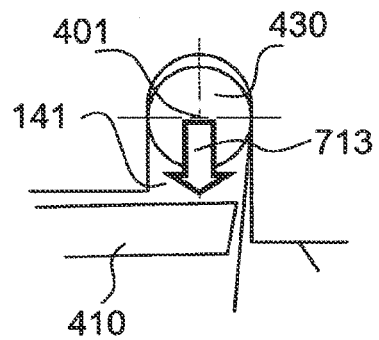
FIG. 14 shows a detail from FIG. 11 in the area of the pivot axis of the actuating lever.

FIGS. 11 to 14 show what happens when the actuating lever 400 is now let go again. The spring 500 was compressed by the actuating movement, during which the legs 501, 502 were moved toward each other. In this way, the spring 500 now exerts an increased restoring force on the actuating lever 400. This restoring force presses the actuating lever back in the direction of its initial position. As is shown in FIGS. 12 to 14, the teeth 421 of the actuating lever 400 slide over the toothing of the plunger rods 310, 320 counter to the direction of advance. The plunger rods are prevented from effecting a return movement by the blocking elements, which are spring-loaded upward in the direction 714. To ensure that the teeth 421 are able to slide over the toothing 321 of the plunger rod, the pivot axis 401 of the actuating lever 400 migrates downward in the direction 713 within the recess 141. In this way, the actuating lever 400 moves back to the initial position in FIGS. 3 to 6. The metering dispenser is now ready for a further dispensing procedure.

While the invention has been explained on the basis of an illustrative embodiment, a great many modifications are of course possible without departing from the scope of the invention. Thus, in particular, the connection between the base unit 100 and the actuating lever 400 can be designed differently. Instead of being received in a recess 141 open toward the bottom, the pivot axis of the lever 400 can also be arranged, for example, in an upwardly and downwardly closed oblong hole extending vertically or obliquely with respect to the direction of advance. The roles of pivot axis and oblong hole can also be changed around, with a suitable oblong hole being formed on the lever 400 and a matching pin being formed on the base unit 100. In this configuration too, the lever as a whole is displaceable between an engagement position, in which the teeth of the lever 400 are in engagement with the toothing 321 of the advancing element 300, and a decoupled position, in which the teeth 421 of the lever 400 are disengaged from the toothing 321 of the advancing element 300.

The spring 500 can of course also be differently designed and, for example, can have one or more helical windings in order to increase the attainable spring force. Instead of a single spring that presses the actuating lever 400 both forward and also upward, separate springs can also be provided for these purposes.

Of course, the return stop mechanism can also be designed in a different way than with the blocking elements shown here. Numerous embodiments for suitable return stop mechanisms are available in the prior art.

A push-in guide element 200, as was used in the embodiment set out above, is not essential, and the advancing element 300 can also be guided in another way than by an insert. Thus, for example, guide structures can be formed directly in the main body 140.

The advancing element itself can likewise have a form different than the one shown here. In particular, the toothing of the advancing element does not need to be formed on the actual plunger rods, and instead it is also conceivable for a toothing to be present on an area that is designed separately from the plunger rods, extends parallel to the plunger rods and is connected to them. In this way, other designs are possible, e.g. also shorter designs than the one shown here.

In the present example, the syringe bodies 110, 120 are connected like a cartridge and are formed integrally with the main body 140 and with the handle 150. While this permits particularly inexpensive production, such a design is not by any means essential, and the syringe bodies can be designed as individual parts or can be designed jointly as a cartridge separate from the main body. The connection between the main body and such a cartridge can be configured, for example, in the manner specified in U.S. Pat. No. 5,336,014.

The connection area 130 at the distal end of the syringe bodies 110, 120 can of course also be designed differently than is shown here, for example via a simple plug connection with Luer connectors, or a mixer can be connected directly and non-releasably to the syringe bodies 110, 120.

Instead of two syringe bodies 110, 120, it is also possible for just one syringe body to be present for dispensing a single component, or it is also possible for more than two parallel syringe bodies to be present. The containers for receiving the components do not necessarily have to be designed as syringes, and instead they can also comprise, for example, a deformable bag or a receptacle like a concertina bellows.

Many other modifications are possible.

LIST OF REFERENCE SIGNS 1 metering dispenser
100 base unit
110 first syringe body
120 second syringe body
121 second syringe plunger
130 fastening area
140 main body
141 recess
142 bottom edge
143 front edge
150 handle
151 fastening location
200 guide element
210 first guide opening
211 first access opening
220 second guide opening
221 second access opening
222 blocking element
230 partition wall
300 advancing element
310 first plunger rod
320 second plunger rod
330 connection area
331 reinforcement wall
400 actuating lever
401 pivot axis
410 main plate
411 top face
412 rear face
420 carrier
421 teeth
430 shaft element
440 actuating area
441 fastening location
500 spring
501 first arm of spring
502 second arm of spring
600 mixer
610 proximal fastening area
620 distal fastening area
701-714 directions

The invention claimed is:

1. A dispensing device for dispensing at least one component, comprising:
   a base body;
   an advancing element, which is guided displaceably relative to the base body and is designed to act on a container containing the component such that the component is dispensed from the container by means of an advance of the advancing element in a distal direction of advance, wherein the advancing element has a toothing along the direction of advance;

an actuating lever having one or more teeth for engagement with the toothing of the advancing element, the actuating lever and the teeth together forming a rigid, dimensionally stable unit, the actuating lever being pivotable relative to the base body from an initial position into an activated position about a pivot axis to advance the advancing element in the distal direction, and the pivot axis being displaceable relative to the base body toward the toothing and away from the toothing for displacing the actuating lever as a whole between an engagement position, in which the teeth of the actuating lever are in engagement with the toothing of the advancing element, and a decoupled position, in which the teeth of the actuating lever are disengaged from the toothing of the advancing element, so as to disengage the teeth from the toothing when the actuating lever returns from the activated position to the initial position.

2. The dispensing device as claimed in claim 1, wherein the actuating lever, with respect to the pivoting movement, is spring-loaded in the direction of the initial position.

3. The dispensing device as claimed in claim 1, wherein the pivot axis is spring-loaded in the direction of the engagement position.

4. The dispensing device as claimed in claim 1, wherein the dispensing device comprises a spring, which generates a first force component in order to load the actuating lever with respect to the pivoting movement in the direction of the initial position, and which generates a second force component in order to load the pivot axis in the direction of the engagement position.

5. The dispensing device as claimed in claim 1, wherein the dispensing device has a return stop mechanism, which impedes a movement of the advancing element-counter to the direction of advance when the actuating lever is moved back from the activated position to the initial position.

6. The dispensing device as claimed in claim 1, wherein the toothing of the advancing element is composed of asymmetrically configured teeth, wherein the teeth have a front flank, which faces in the direction of advance, and a rear flank, which faces in a direction counter to the direction of advance, wherein the front flank assumes a shallower angle to the direction of advance than the rear flank.

7. The dispensing device as claimed in claim 6, wherein the rear flank assumes an angle of more than 90° to the direction of advance.

8. The dispensing device as claimed in claim 1, wherein the base body has a handle shaped like a pistol grip and designed to be grasped in one hand by a user, and wherein the actuating lever has a grip area designed to be pulled by one or more fingers of this hand in the direction of the handle, in order to pivot the actuating lever from the initial position to the activated position.

9. The dispensing device as claimed in claim 8, wherein the teeth of the actuating lever are arranged, with respect to the pivot axis, on a top face of the actuating lever lying opposite the grip area, and the toothing of the advancing element is arranged on an underside of the advancing element facing toward the handle.

10. The dispensing device as claimed in claim 1, wherein a shaft element of the actuating lever is guided displaceably in at least one oblong hole of the base body, in order to move the actuating lever as a whole between the engagement position and the decoupled position.

11. The dispensing device as claimed in claim 1, which comprises at least one cylindrical syringe body for receiving the at least one component, and at least one syringe plunger movable in the syringe body, and wherein the syringe plunger can be pushed forward in the syringe body by the advancing element in order to dispense the component.

12. The dispensing device as claimed in claim 11, wherein the syringe body is designed integrally with the base body.

13. The dispensing device as claimed in claim 11, with at least a first cylindrical syringe body, a first syringe plunger movable therein, a second cylindrical syringe body arranged parallel to the first syringe body, and a second syringe plunger movable in the second cylindrical syringe body, in order to dispense a respective component from each of the syringe bodies.

14. The dispensing device as claimed in claim 13, wherein the advancing element comprises:

a first plunger rod, which acts with a distal end on the first syringe plunger;

a second plunger rod, which acts with a distal end on the second syringe plunger;

a connection area between the plunger rods, which connection area is formed in a proximal end area of the plunger rods in order to connect the plunger rods;

wherein the toothing of the advancing element is formed both on the first and also on the second plunger rod.

15. The dispensing device as claimed in claim 1, additionally having a guide element, which is designed separately from the base body and can be secured on the base body, and in which the advancing element is guided displaceably.

* * * * *